US011495987B2

(12) United States Patent
Fried et al.

(10) Patent No.: US 11,495,987 B2
(45) Date of Patent: Nov. 8, 2022

(54) WIRELESS RECHARGING DEVICES AND METHODS BASED ON THERMAL BOUNDARY CONDITIONS

(71) Applicant: Medtronic, Inc., Minneapolis, MN (US)

(72) Inventors: Andrew T. Fried, St. Paul, MN (US); Venkat R. Gaddam, Plymouth, MN (US); Brett Otteson, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 144 days.

(21) Appl. No.: 16/882,179

(22) Filed: May 22, 2020

(65) Prior Publication Data

US 2021/0367444 A1    Nov. 25, 2021

(51) Int. Cl.
| | | |
|---|---|---|
| *H02J 7/00* | (2006.01) | |
| *H02J 7/02* | (2016.01) | |
| *H02J 50/20* | (2016.01) | |
| *A61N 1/372* | (2006.01) | |
| *H02J 50/80* | (2016.01) | |
| *A61N 1/378* | (2006.01) | |
| *H02J 50/10* | (2016.01) | |

(52) U.S. Cl.
CPC ............ *H02J 7/02* (2013.01); *A61N 1/3787* (2013.01); *A61N 1/37223* (2013.01); *H02J 7/0047* (2013.01); *H02J 50/10* (2016.02); *H02J 50/20* (2016.02); *H02J 50/80* (2016.02)

(58) Field of Classification Search
USPC .................. 320/106, 107, 108, 109, 110
See application file for complete search history.

(56) References Cited

U.S. PATENT DOCUMENTS

| | | |
|---|---|---|
| 9,225,190 B2 | 12/2015 | Labbe et al. |
| 10,322,288 B2 | 6/2019 | Kallmyer et al. |
| 2003/0120271 A1 | 6/2003 | Burnside et al. |
| 2005/0075694 A1 | 4/2005 | Schmeling |
| 2009/0024347 A1 | 1/2009 | Chandra et al. |
| 2012/0262108 A1 | 10/2012 | Olson et al. |
| 2013/0154553 A1 | 6/2013 | Steele |
| 2013/0289662 A1* | 10/2013 | Olson ............... H02J 50/12 607/61 |

(Continued)

FOREIGN PATENT DOCUMENTS

| | | | |
|---|---|---|---|
| WO | WO-2012174563 A1 * | 12/2012 | ......... A61B 5/14503 |
| WO | WO 2018/046156 | 3/2018 | |

(Continued)

OTHER PUBLICATIONS

Antonacci, "Cooling down your wireless power receiver". EDN Network, Jul. 25, 2012, 7 pgs.

(Continued)

*Primary Examiner* — Brian Ngo
(74) *Attorney, Agent, or Firm* — Patterson Thuente Pedersen, P.A.

(57) ABSTRACT

Devices and methods described herein facilitate rapid wireless recharging, while reducing risk of injury, damage, or discomfort caused by heat generated during recharging. The embodiments described herein are useful in a variety of context, including for IoT devices, personal electronics, electric vehicles, and medical devices, among others.

18 Claims, 8 Drawing Sheets

(56) References Cited

U.S. PATENT DOCUMENTS

| | | | |
|---|---|---|---|
| 2015/0008761 A1* | 1/2015 | Kesler | H02J 50/50 |
| | | | 307/104 |
| 2015/0073509 A1 | 3/2015 | Kallmyer | |
| 2016/0146674 A1 | 5/2016 | Reischl et al. | |
| 2016/0294219 A1 | 10/2016 | Van Wageningen et al. | |
| 2018/0159361 A1 | 6/2018 | Cong et al. | |
| 2018/0333585 A1* | 11/2018 | Gaddam | A61N 1/37252 |
| 2018/0345025 A1 | 12/2018 | Stinauer | |
| 2019/0190296 A1* | 6/2019 | Paralikar | H02J 7/007192 |
| 2019/0334367 A1 | 10/2019 | Scott et al. | |
| 2021/0121707 A1* | 4/2021 | Fried | A61N 1/37252 |
| 2021/0212586 A1* | 7/2021 | Iyer | A61N 1/3758 |
| 2021/0393968 A1* | 12/2021 | Monson | A61N 1/3787 |
| 2021/0399584 A1* | 12/2021 | Monson | A61N 1/3787 |

FOREIGN PATENT DOCUMENTS

| | | | |
|---|---|---|---|
| WO | WO 2018/084978 | 5/2018 | |
| WO | WO 2019/118001 | 6/2019 | |
| WO | WO-2019211770 A1 * | 11/2019 | G01K 1/165 |

OTHER PUBLICATIONS

Lord Fulfillment, "Potting and Encapsulant Materials". Accessed Dec. 13, 2019, 12 pgs.

Wolf, "Indwelling Neural Implants: Strategies for Contending with In Vivo Environment". Excerpt of Chapter 3, CRC Press 2008, 20 pgs.

Zhao et al., "Studies in RF Power Communication, SAR, and Temperature Elevation in Wireless Implantable Neural Interfaces", PLoS ONE 8(11): e77759. doi: 10.1371/journal.pone.0077759, Nov. 6, 2013, 11 pgs.

Zhang et al., "An Overview on Thermal Safety Issues of Lithium-ion Batteries for Electric Vehicle Application," IEEE Special Section on Battery Energy Storage and Management Systems, 6: 23848-23863 (May 16, 2018).

Wang et al., "A review of lithium ion battery failure mechanisms and fire prevention strategies," Progress in Energy and Combustion Science. 73:95-131 (2019).

ISO 14708-3. "Implants for surgery: Active implantable medical devices, Part 3: Implantable neurostimulators," 11 pages (Apr. 2017).

International Search Report and Written Opinion for PCT/US2021/070600, dated Aug. 25, 2021, 15 pages.

* cited by examiner

WIRELESS RECHARGING DEVICES AND METHODS BASED ON THERMAL BOUNDARY CONDITIONS

FIELD

The present technology is generally related to wireless recharging. In embodiments, wireless recharging of devices or systems can be managed to regulate heat transferred to adjacent systems.

BACKGROUND

Wireless recharging is increasingly important in systems across a variety of technical fields. For example, wirelessly recharged phones or other devices are increasingly common, and other systems such as electric cars or Internet of Things (IoT) devices arranged throughout a residence or business require a supply of electric charge that is inconvenient to provide via wired connections. One field in which wired electrical power is particularly difficult to provide is that of implantable medical devices, which can serve to provide medical treatment for years without the opportunity for easy wired recharging.

At a basic level, wireless recharging requires only two parts: an emitter and a receiver. The emitter provides a varying electromagnetic field, which is harnessed by the receiver to create a charge current. The charge current can be used either to directly do some work (such as providing medical treatment) or to charge or recharge a battery coupled to the receiver.

Converting electromagnetic signal into charge current inherently generates some level of heating. Often, operation of the device that is being charged or recharged generates additional heating. Depending on the device, there can be maximum safe temperatures. For example, overheating a battery can cause damage or thermal runaway of the battery. In addition to damaging the device itself, surrounding materials or environment may be heat sensitive. This is especially true for medical devices, in which overheating can cause injury or discomfort to the patient.

Conventionally, overheating has been modeled to determine a safe charge current level that, in the most extreme conditions, is unlikely to cause damage to the device or surrounding environment in a majority of cases. Based on such modeling, the total charge current can be capped at what is determined to be a safe threshold. This is not ideal, however, for many systems because the design is constrained from high charge current levels and accompanying fast charging times due to the cap, even in circumstances where faster charging would not be injurious or damaging. Often these caps are set quite low because, if they were raised to make charging more time-efficient, the resulting damage or injury would be significant.

Depending upon the complexity of the device and how critical prevention of overheating is, temperature sensors may be included therein. Temperature sensors provide more flexibility than would otherwise be available for thermal management, because they can be used, for example, to detect a temperature threshold at which the device or surrounding elements will be damaged if it is heated further. When temperature outside the device is of paramount, however, such as for medical devices, conventional temperature sensors are of limited use because temperatures inside the device are not necessarily the same as those outside, which is the primary area of concern for patient safety and comfort.

SUMMARY

In one aspect, a wirelessly recharged device includes a plurality of temperature sensors each arranged within a housing; a coil electrically coupled to a battery, wherein the coil is configured to provide a level of charge current to the battery upon receiving an electromagnetic field; and a processor. Each of the plurality of temperature sensors is electronically coupled to the processor to provide temperature data. The processor is configured to determine the level of charge current and operate a coil based upon a temperature model generated from the level of charge current and the temperature data from the plurality of temperature sensors.

The coil operated by the processor can be the coil electronically coupled to the battery. The plurality of temperature sensors can include at least four sensors. The processor can be configured to receive data via the telemetry coil regarding at least one temperature sensed by an emitter. The term "coil" is used herein to describe several embodiments, but it should be understood that the techniques described herein are based on communications that can take place through an antenna, whether that takes the form of a coil or some other physical structure that would be capable of transmitting signals.

According to another embodiment, a wireless recharge system includes a wirelessly rechargeable device including a plurality of temperature sensors each arranged within a housing. The system can further include a receiver coil electrically coupled to a battery, wherein the receiver coil is configured to provide a level of charge current to the battery upon receiving an electromagnetic field. The telemetry coil can be configured to send and receive data. The system further includes a processor wherein each of the plurality of temperature sensors is electronically coupled to the processor to provide temperature data. The processor is configured to determine the level of charge current, and operate a coil based upon a temperature model generated from the level of charge current and the temperature data from the plurality of temperature sensors. The emitter includes a coil configured to generate a varying electromagnetic field, and a telemetry coil configured to receive the signal from the telemetry coil of the wirelessly rechargeable device.

In embodiments, the plurality of temperature sensors comprises at least four sensors. In embodiments, the emitter includes a plurality of temperature sensors, and the telemetry coil of the emitter is configured to send data corresponding to each of the plurality of temperature sensors of the emitter to the telemetry coil of the wirelessly rechargeable device. The model can be based on the temperature sensed by the plurality of temperature sensors of the emitter and the plurality of temperature sensors of the wirelessly rechargeable device.

In another embodiment, a method of wirelessly recharging a device includes detecting a temperature at a temperature sensor within a wirelessly rechargeable device, determining a model for heat dissipation around the wirelessly rechargeable device, wherein the model for heat dissipation is based upon time-variant thermal boundary conditions; and determining a charge current level based on the model.

The method can include detecting a temperature within an emitter and transmitting the detected temperature within the emitter to the wirelessly rechargeable device. The model for heat dissipation can be based on both time-variant and time-invariant thermal boundaries.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Systems and methods disclosed herein improve upon conventional wireless recharge systems by autonomously updating thermal management models during use. By updating these models to account for thermal dissipation and the thermal resistivity of the surrounding environment, the temperature within the device and in the surrounding can be managed to prevent damage, discomfort, or injury. Another benefit of these embodiments is that, compared to charge-current-limited, conventional wirelessly recharged devices, the charge current of the disclosed devices can be increased based on what the surrounding thermal conditions will bear. Overall, devices described herein and the methods for using them can result in charging that is faster and less likely to cause injury or damage than equivalent devices without such thermal management.

Figure 1A:
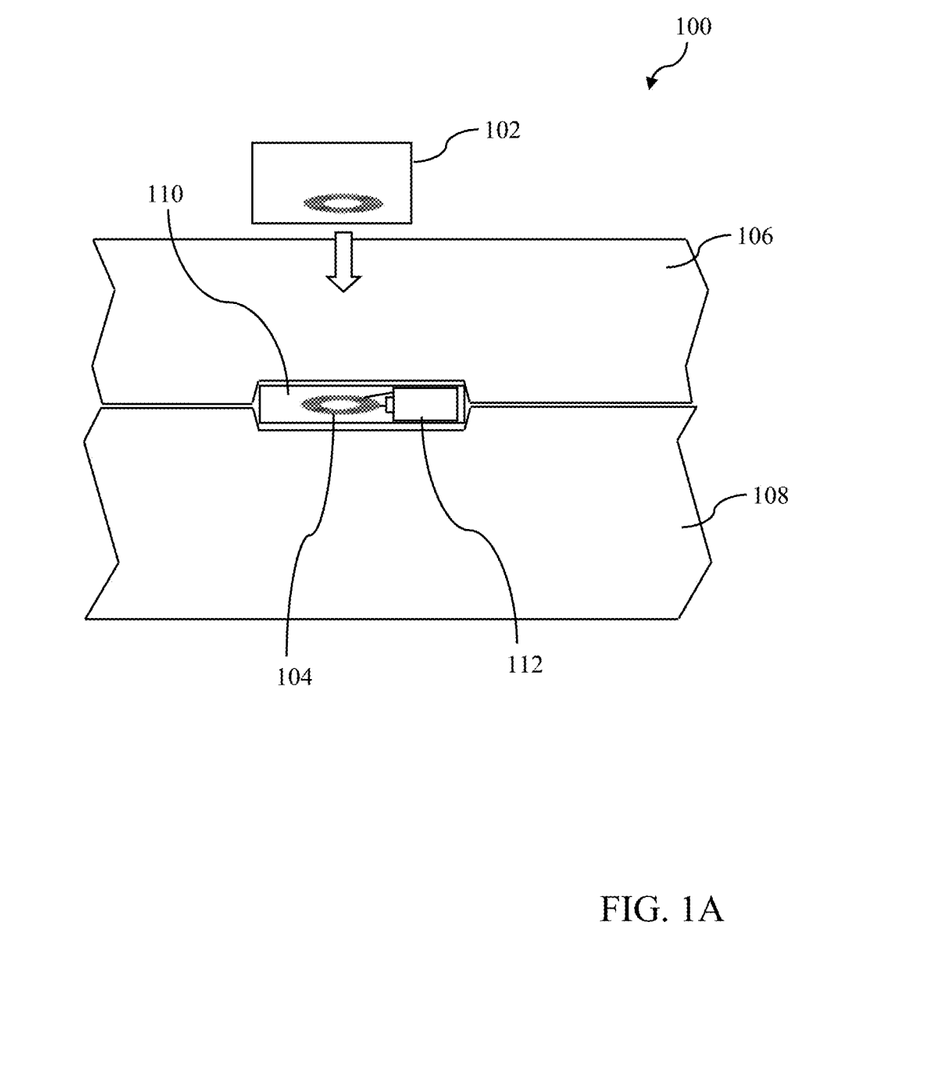
FIGS. 1A and 1B are conceptual diagrams that illustrate a wirelessly recharged system having variable thermal boundary conditions, according to two embodiments.

FIG. 1A shows a system 100 for wireless recharging. As shown in FIG. 1A, system 100 includes two components: an emitter 102 and a receiver 110. Emitter 102 includes a coil that drives an electromagnetic field (shown by the arrow) towards the receiver 110. As described above, it should be understood that emitter 102 could include a coil, as shown in FIG. 1A, or alternatively it could be an antenna or other device for emitting electromagnetic signal in alternative embodiments.

Receiver 110 is shown as surrounded by first material 106 and second material 108 in FIG. 1A. First material 106 has a first set of thermal characteristics and second material 108 has a second set of thermal characteristics. It should be understood that in various recharging environments, there could be one, two, or many different regions with different thermal characteristics surrounding the receiver, or the receiver may be in an "open faced" arrangement wherein it is not surrounded by any material on at least one side, such that the only thermal transfer at that side is convective. The first material 106 and second material 108 are presented solely to enhance understanding of the invention.

As mentioned above, first material 106 and second material 108 can have different thermal characteristics. These thermal characteristics can be, for example, heat capacity, thermal conductivity or other thermal transfer characteristics, or maximum temperatures. In complex systems, such wireless recharging of electric cars, either or both of the first material 106 and second material 108 can be actively controlled, such as by inclusion of heating coils, cooling fluid flowpaths, or other active management systems. In other systems, such as in the medical device field, it is more common that first material 106 and second material 108 would be passive but could have varying thermal characteristics as a function of their material composition (e.g., fat, muscle, bone, skin, or hair each retain or transmit heat differently from one another).

In one embodiment, first material 106 can be scalp while second material 108 can be skull. In another embodiment, first material 106 can be skull and scalp, while second material 108 can be brain. In another embodiment, first material 106 can be subcutaneous fat, while second material 108 can be visceral fat or muscle. In another embodiment, first material 106 could be a patient, and second material 108 can be garments, hair, blankets, or other coverings. In a non-medical context, first material 106 could be the external case of a rechargeable electronic device, while second material 108 could be circuitry or other internal components of the rechargeable electronic device. Depending upon the field of use, the thickness or composition of the first material 106, second material 108, or even additional materials can vary. In yet another embodiment, first material 106 could be the exterior of an electric vehicle, while second material 108 could be a battery.

Figure 2A:
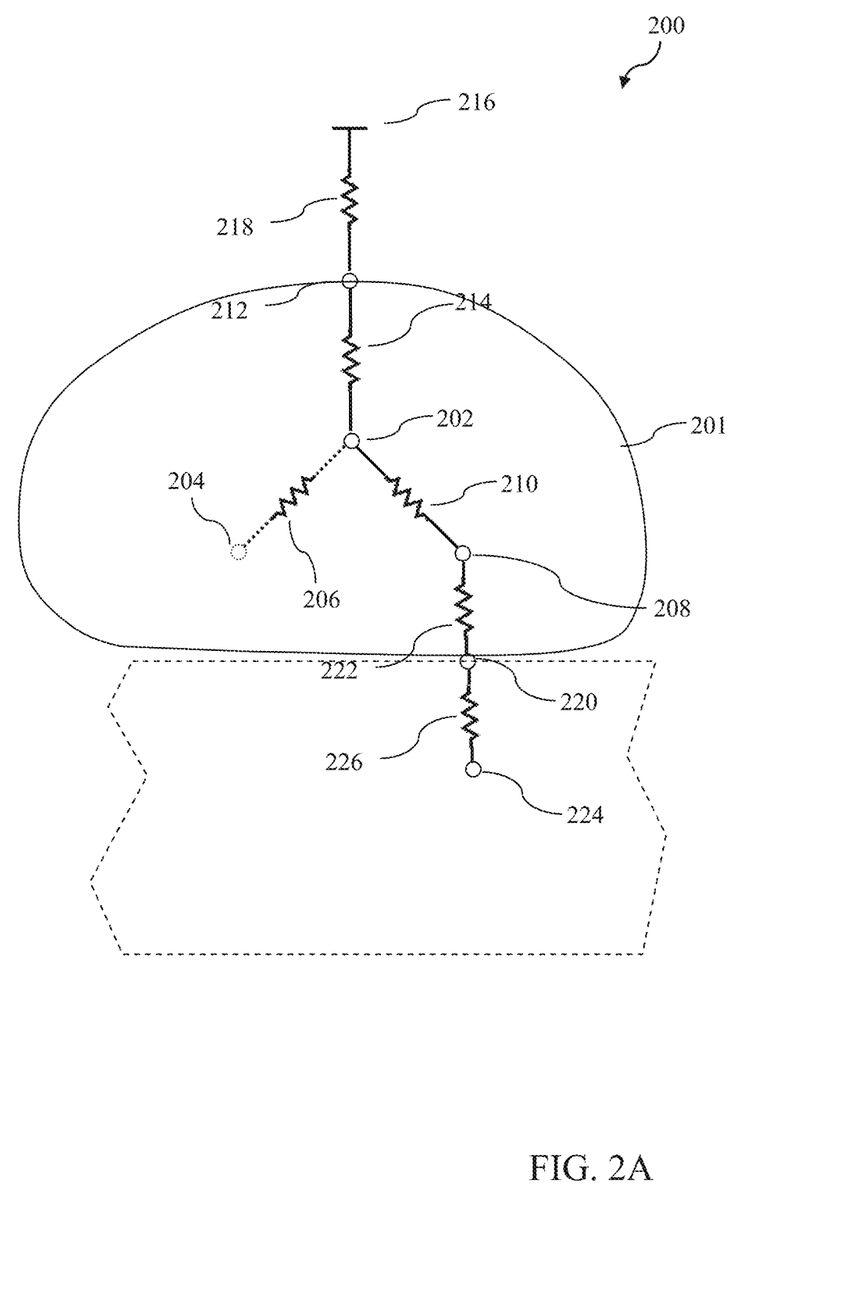
FIG. 2A is a conceptual diagram that illustrates a thermal resistivity model according to an embodiment.

Receiver 104 also varies between embodiments. FIG. 2A shows a simple embodiment in which the receiver 110 includes a receiving coil 104, a rectification circuit 111, and a battery 112. It should be understood that, depending upon the device that receiver 104 is used to charge or operate, there may be additional components, including processors, motors, pumps, telemetry, sensors, and the like. In each embodiment, however, receiver 104 transforms electromagnetic signal emitted by the emitter 102 into usable power via typical use of a rectification circuit 111.

In some embodiments, emitter 102 can have a corresponding power circuit, similar to circuitry 111, which can control the emitter coil to provide modified power output. It should be understood that such circuitry can be operated in addition to or as an alternative to the rectification circuit 111 at the receiver side.

Rechargeable devices are becoming more common in a variety of settings, and large battery storage is increasingly common as well. As these devices and their increasingly large battery storage needs become prevalent, wirelessly recharging them becomes attractive. Large batteries, however, come with larger recharging times, and users of those devices may not be willing to wait for the long recharge times that those devices need. For example, electric vehicles may take several hours to recharge, limiting their adoption compared to those with combustion engines that can be refueled within minutes. In the medical device field, recharging an implanted device can take about 30-90 minutes for many devices, Therefore it would be beneficial for emitter 102 to produce the maximum level of electromagnetic signal that can be used at receiver 104 without some detrimental effect due to overheating the battery (e.g., 112) or the surrounding material (e.g., 106, 108).

During use, therefore, the receiver 104 can model the temperature of itself, of the surrounding materials 106, 108, or both, in embodiments. The temperature model can be updated occasionally or continuously to detect the thermal transfer away from the receiver 104, to modify levels of charge current from the receiver 104 to the battery 112 as needed either by changing the electronic characteristics of the receiver 104 itself, or by sending a signal back to the emitter 102 to reduce or increase the level of electromagnetic signal produced to an appropriate level. In other embodiments, the emitter and control algorithm running in the emitter 102 may have knowledge of the thermal model associated with the receiver and can model the receiver 110 with associated surrounding materials.

Figure 1B:
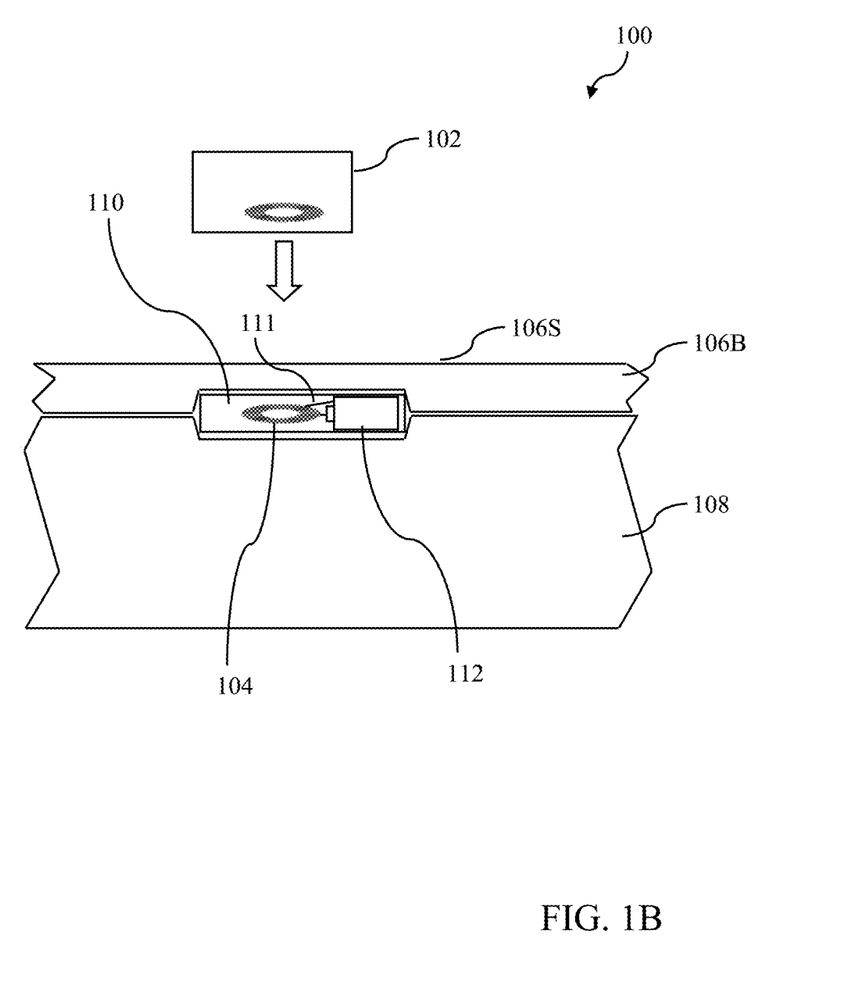

The comparison between FIG. 1A and FIG. 1B illustrates how this model might be adjusted. In FIG. 1B, the same components are shown as described above with respect to FIG. 1A, except for one key distinction. In FIG. 1B, the thickness of the first material (106 in FIG. 1A, 106B in FIG. 1B) is much smaller. Therefore, even if the first material 106 of FIG. 1A has identical thermal characteristics to the first material 106B of FIG. 1B, thermal transfer to the surface 106S of FIG. 1B will be faster due to lower thermal resistance for heat exiting through that surface 106S. In other words, due to its mechanical shape, the thermal resistance of first material 106B of FIG. 1B is lower than the thermal resistance of first material 106 of FIG. 1A.

In the context of a medical device, this type of change can easily occur due to a shift in the location of an implanted device, due to gain or loss of weight by the patient, or due to the donning or doffing of garments, or due to the growth or cutting of hair, for example. Some of these changes impact the depth of the device within the surrounding material (106, 106B), while others involve the addition or removal of another type of material like clothing or hair. Material composition itself can even be affected by hydration levels or subcutaneous fat thickness.

In other contexts, similar changes in material composition or thickness could occur, such as accumulation of dirt or snow on the hood or undercarriage of an electric car, or addition or removal of a new case from a wirelessly rechargeable phone.

In conventional systems, changes in the thermal characteristics of the material surrounding a receiver could result in wireless charging or recharging that is either too fast or too slow. For example, if a good thermal sink is available at surface 106S, and if first material 106 were to become thinner as shown in the comparison between FIGS. 1A and 1B, then thermal resistance between the heat source and the heat sink is reduced and charging could be conducted more quickly without exceeding a temperature threshold that would cause damage, injury, or discomfort. If, on the other hand, the wireless recharging charge current maximum or cap is set assuming a low thermal resistance (as shown in FIG. 1B) which subsequently becomes higher (as shown in FIG. 1A), then heat may build up to an unacceptable level at the receiver 104. Without updates to the thermal model that determines the safe charge current level or safe power level of the emitters, therefore, charge current will often be at a non-optimal level that is either slower than possible or higher than is safe or comfortable. In the context of an electric vehicle, for example, safe charging rates during a cold winter may be significantly higher than safe charging rates during a hot summer day. See, e.g., Jianan Zhang et al., An Overview on Thermal Safety Issues of Lithium-ion Batteries for Electric Vehicle Application, IEEE Special Section on Battery Energy Storage and Management Systems (May 16, 2018); Qingsong Wang et al., A Review of Lithium Ion Battery Failure Mechanisms and Fire Prevention Strategies, 73 Progress in Energy and Combustion Science 95-131 (2019).

FIG. 2 FIG. 2A depicts a thermal model, according to one embodiment. For ease of understanding, the model is shown using symbols more often used in the field of electronics. For example, temperature sensors are depicted as "nodes" (open circles) and materials that create thermal resistance are shown as "resistors" (zig-zagging line sections). This choice of symbology is instructive for a few reasons. First, like a resistor in a Thévenin equivalent circuit, each thermal resistance can be a placeholder for a variety of individual components each having a corresponding thermal transfer rate. Second, like an electronic circuit, embodiments described herein involve the modeling of the system to determine how current will flow. There are some differences between electrical and thermal transfer (e.g., electrical transfer is based on the absolute voltage difference between two nodes separated by a resistor, whereas thermal transfer is based on the ratio of the absolute values of the temperatures of the two portions separated by a thermal resistance). It should be understood that a person having ordinary skill in the techniques of thermal management of devices would understand how to modify the "electric" model to instead apply to thermal modeling, and indeed some examples are provided below to make this transformation clear (for example, compare Equation 3A with Equation 3B, below).

FIG. 2A shows a system 200 according to a medical device embodiment. System 200 includes both a device 201 and a surrounding region. The surrounding region is indicated in FIG. 2A with dashed lines. In the context of an external medical device, such as a charger, the surrounding region in FIG. 2A may be the body with the temperature at node 220 being the skin temperature. Within the device 201 are three temperature sensors separated from one another by some level of internal thermal resistance. In particular, temperature sensor 202 is separated from temperature sensor 204 by thermal resistance 206, while temperature sensor 208 is separated from temperature sensor 202 by thermal resistance 210.

Temperature sensor 204 and thermal resistance 206 are optional components, and are shown in dashed lines. In embodiments, a third temperature sensor 204 and corresponding thermal resistance 206 are useful to form a complete thermal model of heat transfer through device 201 and into the surrounding environment. In other embodiments, the third temperature sensor 204 is not required, such as embodiments in which thermal transfer in one particular direction is of primary interest.

Outside of device 201, additional temperatures are shown, including temperature node 212 which is separated from temperature sensor 202 by thermal resistance 214, temperature node 216 which is separated from temperature node 212 by thermal resistance 218, temperature node 220 which is separated from temperature node 208 by thermal resistance 222, and temperature node 224 which is separated from temperature node 220 by thermal resistance 226. These thermal nodes and resistances, as will be explained in more detail below, are not necessarily measured, and there may not be—and indeed typically is not—a temperature sensor present in every one of these locations. Instead, modeling of temperatures and resistances can be conducted based on the sensed temperatures at the temperature sensors 202 and 208 (and optionally 204) to infer these data in a real-world implementation. From these inferred data, a wireless recharge system can be operated in a way that produces a desirably high level of charge current without exceeding a temperature point that would cause injury or damage.

In various embodiments, a heat source or multiple heat sources can be present within device 201. In almost any wirelessly recharged system, the transfer of electrical current to useful work or to stored charge will create at least some heat. For purposes of the discussion of FIG. 2A it is assumed that there is one source of heat within device 201, and that the source of heat is arranged proximate to temperature sensor 208.

In addition to having any number of sources of heat, it should also be noted that wirelessly charged devices can also have a variety of temperature thresholds that can also be location-specific. For example, in a fast-recharge system for an electric vehicle, the temperature of the battery itself may be important, whereas for a medical device the battery temperature is important, but the exterior temperature of the device is of high importance as well. For purposes of the discussion of FIG. 2A it is assumed that both the interior and exterior temperatures are important and have unique thresholds that should not be exceeded.

Thresholds for the temperature at each part of the device 201 can vary. For example, in a medical device there may be a temperature threshold for the internal components (e.g., proximate to temperature sensors 202, 204, and 208) that is based upon safe operating temperatures for lithium-ion batteries, or to avoid damage to circuitry or materials within the device 201. For exterior temperatures, especially in a medical device context, the predominant concern is patient safety and comfort. Each of these thresholds may have a short-term limit or a long-term limit, or both. For example, a short-term limit for internal temperatures within device 201 could be a temperature at which a lithium-ion battery will suffer from internal overcharge or thermal runaway, while a long-term limit could be a temperature at which the materials that make up device 201 will be damaged if they experience long-term exposure above that temperature. A short-term limit for exterior temperature could be a temperature at which the patient will experience burns, whereas a long-term limit could be a temperature that is uncomfortable with sufficiently long exposure.

Depending upon the type of device 201, detecting that these limits have been exceeded is not currently possible, especially for exterior temperatures. It is not often possible or practicable to position temperatures sensors about the body of a patient, and so medical device makers have conventionally assumed conservative scenarios to ensure that the short-term and long-term limits are not exceeded. These conservative estimates result in a separate problem for those with implantable devices, which is that charge time is correspondingly slower. In addition, in some cases the device may indeed still exceed the long-term or short-term limits, causing discomfort, pain, or injury if charging is not stopped. It is generally recognized that thermal dose thresholds based on time and temperature in excess of a certain number of Cumulative Equivalent Minutes at 43° C. (i.e., CEM43 standards such as ISO 14708-3: 2017, clause 17) can provide guidance for better outcomes and patient safety. For example, ISO 14708-3: 2017 specifies a maximum of 40 minutes CEM43 for muscle and fat and 21 minutes for skin.

These challenges are addressed by a system 200 that includes a number of temperature sensors 202, 204, 208, all within the device 201, and yet all of which are separated from one another and the patient by known thermal resistances 206, 210, 214, 222 such that the temperature of the exterior environment can be modeled more accurately. As a result of this more accurate modeling, charge current or other heat-generating functions of the device 201 can be adjusted to reduce recharge time and ensure a more comfortable, safer recharge.

The model depicted schematically in FIG. 2A incorporates known thermal resistances and behavior of the system at boundary conditions. External temperature 212 is, in the context of a medical device, the temperature of a device facing away from the patient, such as to the ambient environment. The thermal resistance 214 that separates temperature sensor 202 from external temperature node 212 has components that are a function of the device itself (i.e., thermal resistance from the temperature sensor 202 to the outer part of the housing of the device 201) as well as components that are a function of the environment (i.e., such as if the external device is covered by a blanket or furniture, or if it is exposed to cool or warm air, as described above). Therefore, unlike thermal resistances 206, 210, 214, 222, the thermal resistance 218 is not precisely known. Furthermore, thermal resistance 218 is variable, and can change as a function of time. Thermal resistance 218 (and temperature node 216) are used to simulate the effect of surrounding environment for thermal diffusion, which is why in keeping with the electronics analogs, temperature node 216 is shown as "ground." Thermal resistance 218 could be increased by a patient donning heavier clothing, pressing the device 201 against furniture or a thermal insulator, entering a warmer or cooler room, or any other action that increases or decreases the rate at which heat dissipates into the surrounding environment.

Using the model in FIG. 2A, temperatures at key parts of the system 200 can be estimated accurately, even where temperature sensors are not present. For example, in the medical device context, real-time measurements of temperature may only be conducted at 202, 204, and 208, and resistances 206, 210, 214, and 222 may be known while resistances 226 and 218 are unknown. On the other hand, in some embodiments, the system design may assume a fixed value for resistance 226 and temperature 224 according to empirical testing or modeling in order estimate 220 real time.

For example, when a patient is in an environment that is good for heat dissipation, the value of the thermal resistance of thermal resistor 218 is low. In that case, the temperatures at temperature sensor 202 and temperature node 212 are low, because there is little thermal resistance between the device 201 and "thermal ground" 216. Even though temperature may not be directly measured at temperature node 212, this high thermal dissipation will result in a larger temperature difference between temperature sensor 202 and temperature sensor 208. Thermal resistance 210 is constant, and so the total thermal resistance between temperature sensor 202 and thermal ground 216 can be determined. Although thermal resistance 218 can vary slightly over time, it would be unusual to experience large or fast changes in thermal resistance between temperature sensor 202 and temperature node 212, and so it is possible to effectively measure the quantity of heat dissipation, or how thermally diffuse the environment is around the patient. To simplify this problem, we can assume that temperature sensor 204 is not included in the system and thermal resistance 206 is high enough that the heat flux through 206 is negligible. Furthermore, we will assume that temperature 216 is fixed and is lower than that internal to the device, such as near the heat source at 208. Given this assumption, this thermal system can be reduced to equation form:

$$T_{202} = (T_{208} - T_{216}) \frac{R_{214} + R_{218}}{R_{210} + R_{214} + R_{218}} + T_{216} \qquad \text{Eq. 1a}$$

where $T_{202}$ is the temperature at temperature sensor 202, $T_{208}$ is the temperature at temperature sensor 208, $R_{210}$ is the thermal resistance at 210, $R_{214}$ is the thermal resistance at 214, $T_{216}$ is the temperature at 216, and $R_{218}$ is the thermal resistance at 218.

$T_{202}$ and $T_{208}$ of Equation 1 are directly measurable. Furthermore, for a given system, thermal resistance $R_{210}$ and thermal resistance $R_{214}$ can be measured empirically. In embodiments, $R_{214}$ can be assumed to remain constant between updates of an algorithm setting target power of the transmitter, for example. Therefore, the only variable in Equation 1 is thermal resistance $R_{218}$. Accordingly, changes in $R_{218}$ can be determined using Equation 1b. For example, if we assume room temperature (20° C.) for $T_{216}$, measure 30° C. at $T_{208}$, measure 25° C. at $T_{202}$, and know that $R_{214}$ and $R_{210}$ are 2 K/W and 3 K/W, respectively, then $R_{218}$ is computed as 1 K/W. On the other hand, if all other measurements were the same, but $T_{202}$ was measured as 27° C. instead of 25° C., then $R_{218}$ is computed as 5 K/W. So, as the difference in temperature between $T_{208}$ and $T_{202}$ increases, the resistance $R_{218}$ decreases.

$$R_{218} = \frac{-T_{202}(R_{214} + R_{210}) + T_{208} * R_{214} + T_{216} * R_{210}}{T_{202} - T_{208}} \qquad \text{Eq. 1b}$$

Another result of determining changes in thermal resistance $R_{218}$ using Equation 1 is that the temperature at temperature node 212 can be determined based only on the sensed, internal temperatures $T_{202}$ and $T_{208}$. The temperature at temperature node 212, $T_{212}$, can be determined using an equation that also follows directly from the "thermal circuit diagram" of FIG. 2A:

$$T_{212} = (T_{208} - T_{216}) \frac{R_{218}}{R_{210} + R_{214} + R_{218}} + T_{216} \qquad \text{Eq. 2}$$

Inserting known values (or approximations) can therefore be used to determine the temperature at temperature node 212, which or primary importance to the patient to avoid injury or discomfort. The determination can often be made by a simple comparison of $T_{202}$ and $T_{208}$. As described in the example above, when ambient environmental conditions provide for good heat dissipation (i.e., low thermal resistance $R_{218}$), the difference between $T_{202}$ and $T_{208}$ increases. Therefore, a system 200 could be designed to increase or decrease wireless field strength for recharging based upon the difference between these two values.

In one embodiment, a value C can be determined that is a function of $T_{202}$, $T_{208}$, and a heat limit Q. The value C can be set in numerous ways. Some examples are:

$$C = T_{208} - T_{202}; \text{ or} \qquad \text{Eq. 3A}$$

$$C = \frac{T_{208} - T_{202}}{Q} \text{ for } T_{208} > \text{baseline; or} \qquad \text{Eq. 3B}$$

$$C = R_{218}(\text{per Eq. } 1b); \qquad \text{Eq. 3C}$$

In Equation 3B, the baseline can be set based upon a comfort or safety threshold as described above. One baseline temperature that could be used for medical devices, for example, is 39° C. or 41° C. Then, the system could adjust the power output level according to C.

Figure 2B:
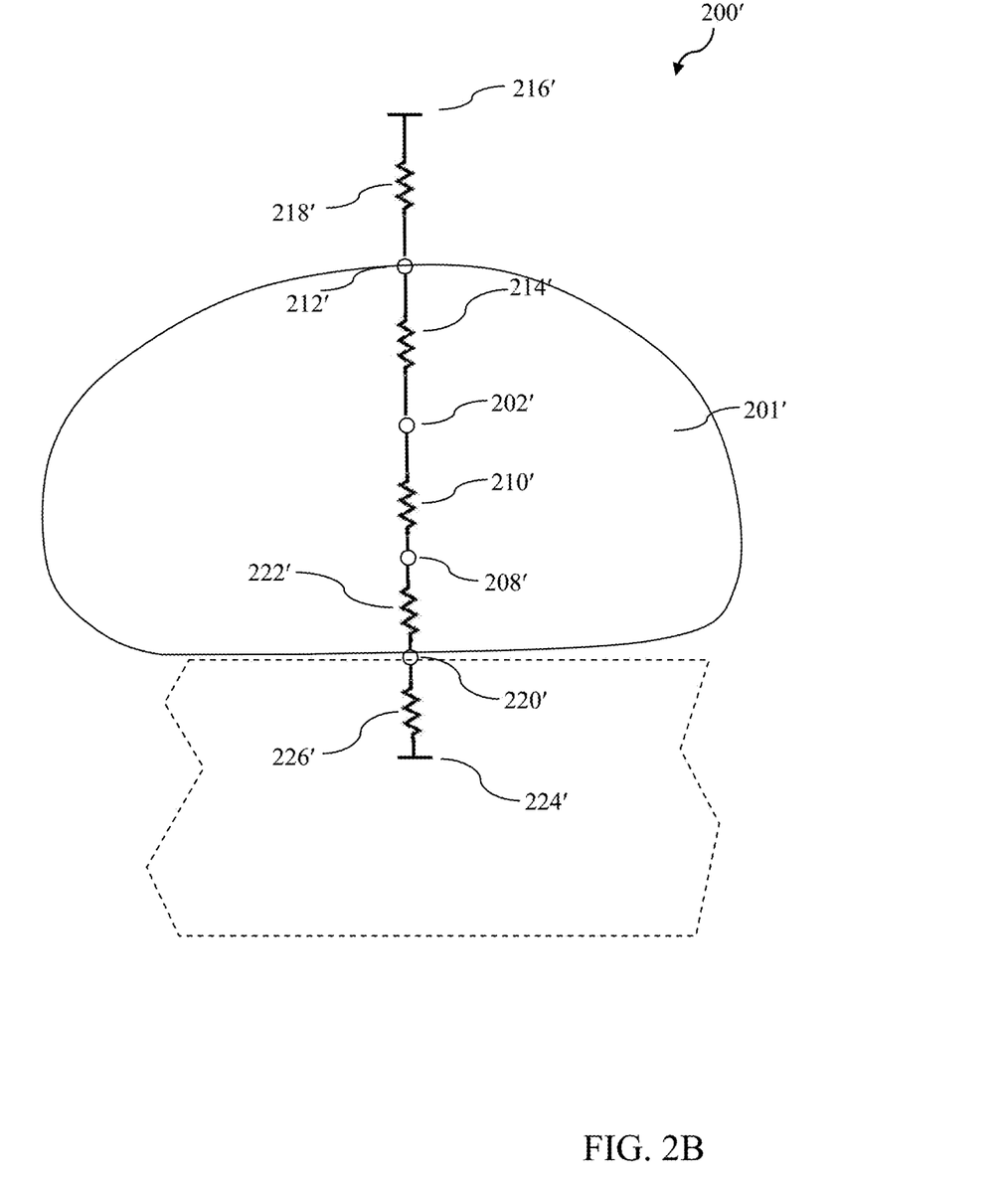
FIG. 2B is a conceptual diagram that illustrates another thermal resistivity model according to an embodiment.

FIG. 2B depicts an alternative embodiment of a thermal model based on a two-sensor design. The elements of FIG. 2B are similar to those previously described with respect to FIG. 2A. Where structures are the same or similar, they are indicated with the same reference numeral and a 'prime' mark thereafter. These components are not described a second time with respect to FIG. 2B, since they will be readily understood by virtue of the description of their counterparts in FIG. 2A.

As shown in FIG. 2B, a thermal resistance model is created for a heat source (in the device 201') located at a position between a thermal sink (224') and an external environment (216'). Heat dissipation to either 224' or 216' is modeled based upon a thermal resistance (shown here as an electrical resistance) that depends upon the ambient conditions. For example, where device 201 is an implantable medical device, the thermal dissipation through a conductive environment towards sink 224' may be slower than thermal dissipation through a convective environment towards sink 216' in some circumstances, and lower in others. The rate of change of the thermal resistances 210', 214', 218', and 226' can also be relatively constant as a function of time, or they can be variable as a function of time, as described above with respect to FIG. 2A.

FIG. 2B is a two-sensor embodiment in that only nodes 202' and 208' are temperature sensors, similar to the assumptions in the example which led to Equations 1a and 1b. The rest of the nodes (212' and 220') are modeled based on detected heat flow. For example, temperature at node 220' can be modeled as $$T_{220'} = \frac{R_{226'}}{R_{226'} + R_{222'}}(T_{208'} - T_{224'}) + T_{224'}$$

$$T_{220'} = k_{Applied}(T_{208'} - T_{224'}) + T_{224'}$$

$R_{218}$ and $T_{216}$ can vary significantly as a function of time in most types of rechargeable devices, while the other resistances and temperatures change more slowly (if at all). The unknown elements, therefore are $T_{212'}$, $T_{216'}$, and $R_{218'}$, and these temperatures and resistance together define the amount of heat dissipated convectively, $Q_{ENV}$. Specifically, $$\frac{T_{212'} - T_{216'}}{R_{218'}} = Q_{ENV}$$

Continuing with the analogy to electrical current, Kirchoff's laws dictate that all of the "currents" from each node sum to zero. Heat values such as $Q_{ENV}$ are analogs to current in the circuit shown in FIG. 2B, and indeed at steady state (or thereabouts) the net heat traveling into or out of a particular region of the device 201' will be zero. As shown in FIG. 2B, all of these resistances are in series, such that $Q_{ENV}$ is the same as heat traveling between nodes 208' and 202'. That is, $$Q_{ENV} = Q_{210'} = \frac{T_{208'} - T_{202'}}{R_{210'}}$$

Therefore $Q_{ENV}$ can be calculated from known values. Furthermore, $T_{212'}$ can be calculated based the determined resistances and temperatures. In other words, the recharge system including only two temperature sensors can determine the heat sunk to the environment convectively, and a temperature on the convective-facing surface, when the device 201' is at steady thermal state.

In one example, when the device 201' is used outside on a cold day and the convective side (i.e., the top side with respect to the orientation on the page of FIG. 2B) is exposed to air, $Q_{ENV}$ will be quite high and can be sensed because $T_{202'}$ will be much lower than $T_{208'}$. Conversely, when the air temperature increases, $Q_{ENV}$ would be low because $T_{202'}$ would not be much lower than $T_{208'}$. This determination of $Q_{ENV}$ and surface temperature enables an adaptive algorithm to vary the heat dissipation limit of the device 201' depending on the conditions in the external environment. That is, the recharge system could operate at higher heat dissipation levels with $Q_{ENV}$ is sensed to be high, increasing recharge area and depth for implantable medical devices or enabling faster recharge of other devices in cold or especially convective conditions.

Figure 3:
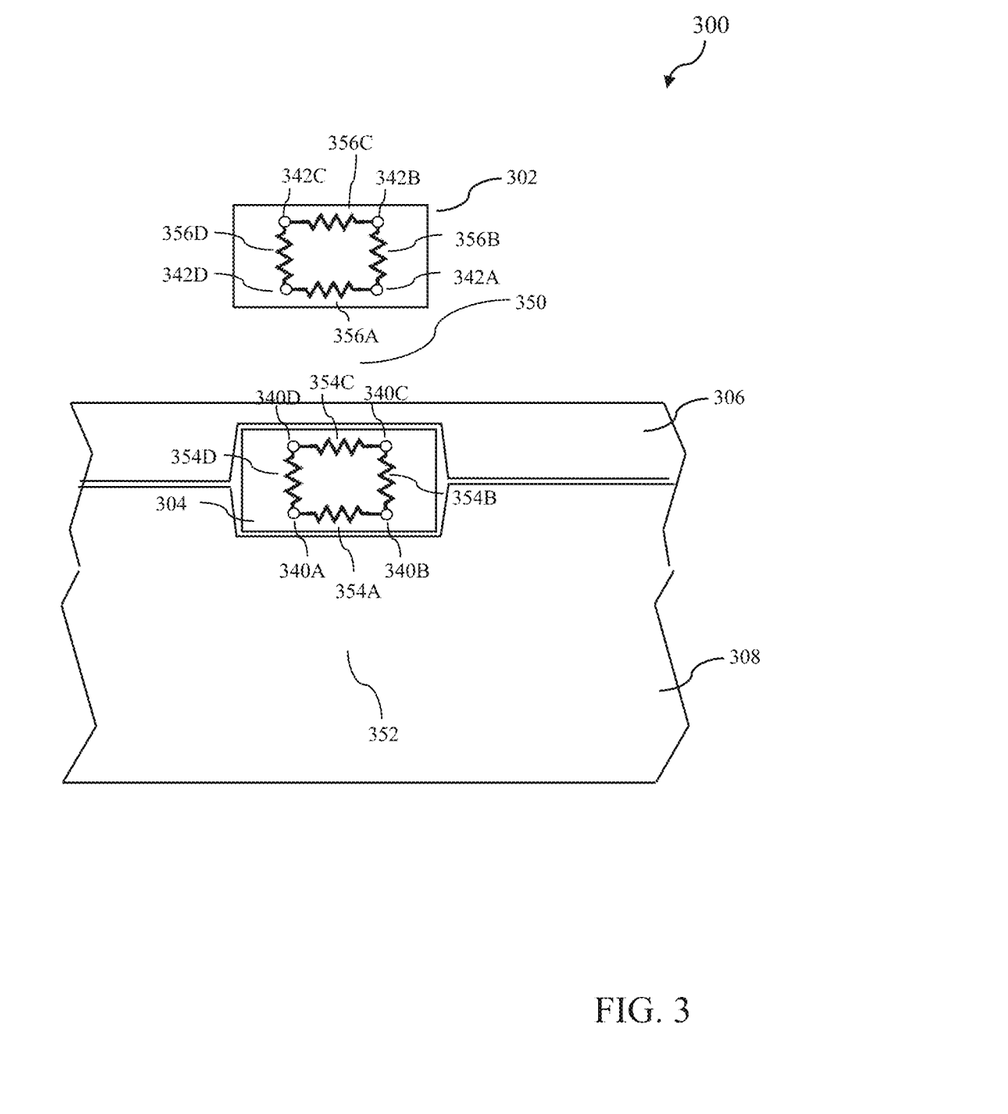
FIG. 3 is a schematic of a wireless recharging system according to an embodiment.

FIG. 3 is a simplified schematic of another embodiment, including a larger number of temperature sensors configured to detect thermal characteristics of an environment. Like the description of FIG. 2A, the detailed description of FIG. 3 relates to medical devices, but it should be understood that thermal management is relevant to a wide array of wirelessly recharged devices and systems, and the methods and systems described herein are not limited to implantable or implanted devices or indeed to the medical device field whatsoever.

Reference numbers used in FIG. 3 are used to describe similar structures to those previously described with respect to FIGS. 1A and 1B. When a similar structure is shown, the reference number for that part is iterated by a factor of 100. For example, first material 306 and second material 308 are similar to first material 106 and second material 108 of FIGS. 1A and 1B.

The structure shown in FIG. 3 is somewhat more sophisticated than the structures shown in FIGS. 1A and 1B, in that FIG. 3 shows both an emitter 302 and a receiver 304 that include four temperature sensors. In particular, emitter 302 includes temperature sensors 342A, 342B, 342C, and 342D, while receiver includes temperature sensors 340A, 340B, 340C, and 340D. The temperature sensors in each of the emitter 302 and receiver 304 are separated from one another by knowable thermal resistivities. The thermal resistivities between the pairs of temperature sensors are shown in FIG. 3 as resistivities 354A, 354B, 354C, and 354D (in the receiver 304) and 356A, 356B, 356C, and 356D (in the emitter 302).

With the known temperatures at each of the temperature sensors 340A-340D and 342A-342D, a model for the surrounding environment can be created similar to the model described in FIG. 2A. The model created in this way can be used to estimate the flow of heat in and out of region 350, in between the emitter 302 and receiver 304, as well as region 352, opposite the receiver 304 from the emitter 302.

In a medical device context, each of these regions can have different thermal requirements. For example, in an implanted neuro-stimulation device, the region 352 can be a skull or brain material, while the region 350 can be a scalp region. Each of these regions 350, 352 can have different maximum acceptable temperatures before injury or discomfort will occur. Furthermore, the transfer of heat will vary by patient, such as by skull thickness, size of the device (and corresponding amount of skull removed), etc.

Regions 350 and 352 differ also in the type of heat diffusion environment. In the context of a neuro-stimulation implant, the thermal resistivity of region 352 will not vary significantly over time, since skull thickness and maximum acceptable brain temperature do not vary. On the other hand, the heat transfer through region 350 could vary significantly, depending on the patient's environment, clothing, and hair. Therefore, the model described in FIG. 2A can be adjusted to account for both types of heat-transfer boundaries (variable and invariable).

In steady state, $$Q_{INS} = Q_{TOP} + Q_{BOT} \quad \text{Eq. 4}$$

where $Q_{INTs}$ is heat in the device, $Q_{TOP}$ is heat through the top, and $Q_{BOT}$ is heat through the bottom of the implantable device. $Q_{TOP}$ may be defined as $$Q_{TOP} = \frac{\frac{T_{340D} + T_{340C}}{2} - \frac{T_{342D} + T_{342A}}{2}}{R_{skin}} \quad \text{Eq. 5}$$

where Rskin is an empirically modeled thermal resistance having units of K/W and is a thermal property of region 350.

Likewise, $Q_{BOT}$ can be defined as $Q_{INS} - Q_{TOP}$ (see Eq. 4), and therefore $$\frac{\frac{T_{342D} + T_{342A}}{2} - T_{BRAIN}}{Q_{BOT}} = R_{skull}$$

where $R_{skull}$ is a thermal property of region 352.

Modeling the thermal properties of skin and skull in this way, while only requiring thermal measurements from within the device where they are easily detectable, provides for improved controllability of thermal output at each region of interest. Devices using these modeling systems can therefore achieve higher charge current when local conditions allow, without sacrificing patient comfort or causing undue risk of injury from higher charging heat.

Figure 4:
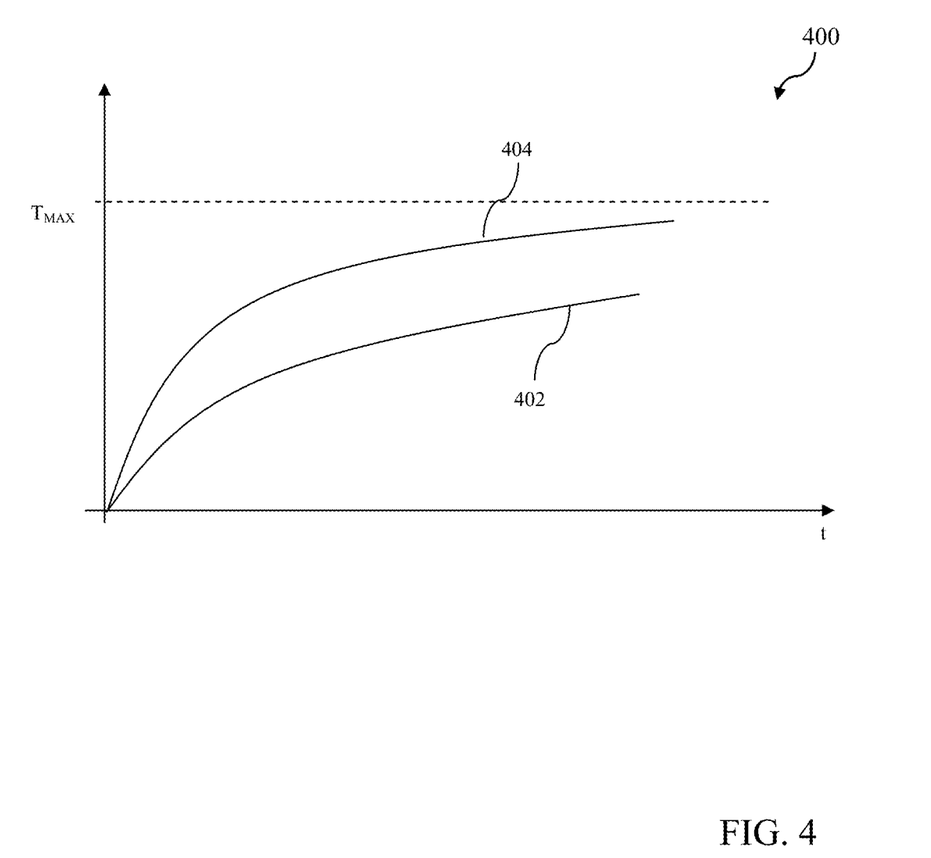
FIG. 4 is a chart of temperature as a function of time according to two thermal models, in an embodiment.

FIG. 4 is a chart 400 of temperature as a function of time in region 352 in two patients using the same level of recharge field and corresponding recharge current. The temperature shown on the y-axis is the temperature in the brain of the patient adjacent the skull. First line 402 corresponds to a patient with a low thermal transfer through the skull to the brain, whereas second line 404 corresponds to a patient with a high thermal transfer through the skull (i.e., low thermal resistance $R_{352}$). As shown in FIG. 4, the patient associated with first line 402 (which has high resistance $R_{352}$, between the device and the brain) can be exposed to the heat level for a longer time period than the patient associated with second line 404 before risking exceeding $T_{MAX}$, the highest temperature that is considered safe. By determining the thermal transfer characteristics of the patient, therefore, the charge time (or charge current level) can be adjusted to maintain safety and comfort while improving upon charging speed in many cases.

Figure 5:
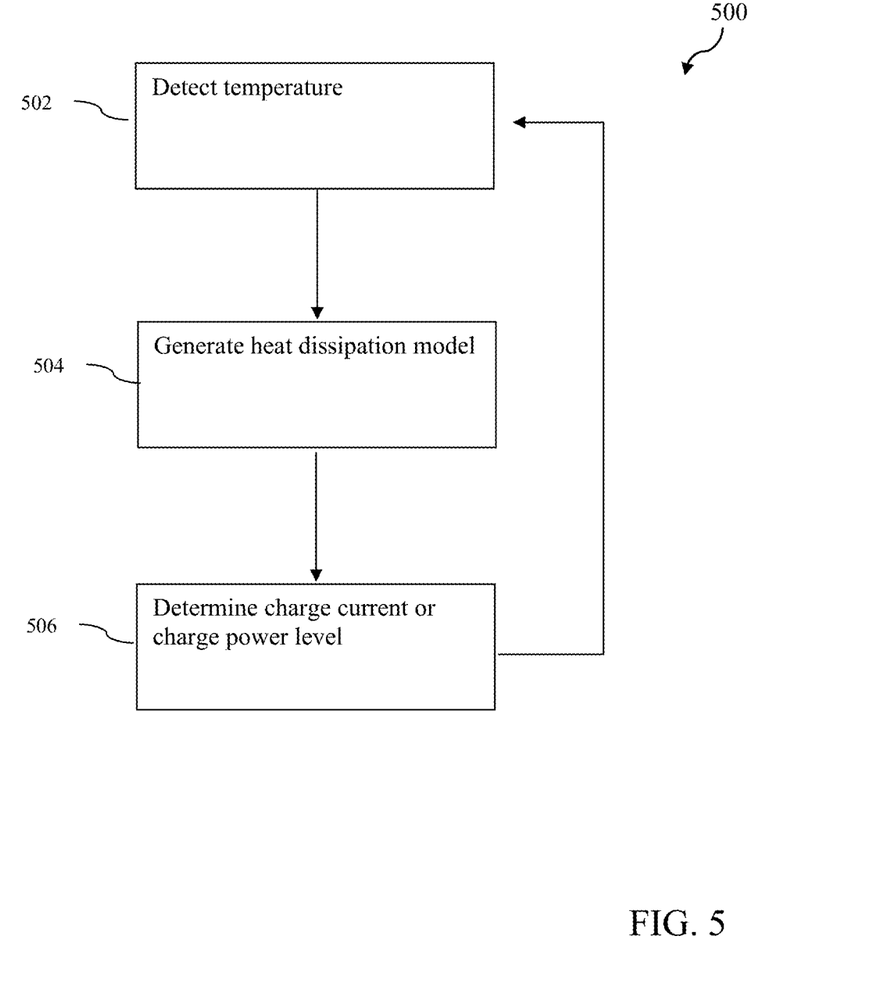
FIG. 5 is a flowchart of a method for operating a wirelessly recharged system using a thermal management technique according to an embodiment.

FIG. 5 is a flowchart of a method 500 for operating a system as described above. According to the method 500, at least one temperature is detected at 502. The detected temperature, as described above, can be used to generate a heat dissipation model 504. The heat dissipation model can then be used to set a charge current or charge power level at 506. The charge current or power level 506 may be increased or decreased, for example, or in some embodiments the absolute charge power level may be set at a predetermined value and the level can be toggled between "on" and "off" states based on the heat dissipation model generated at 504.

Figure 6:
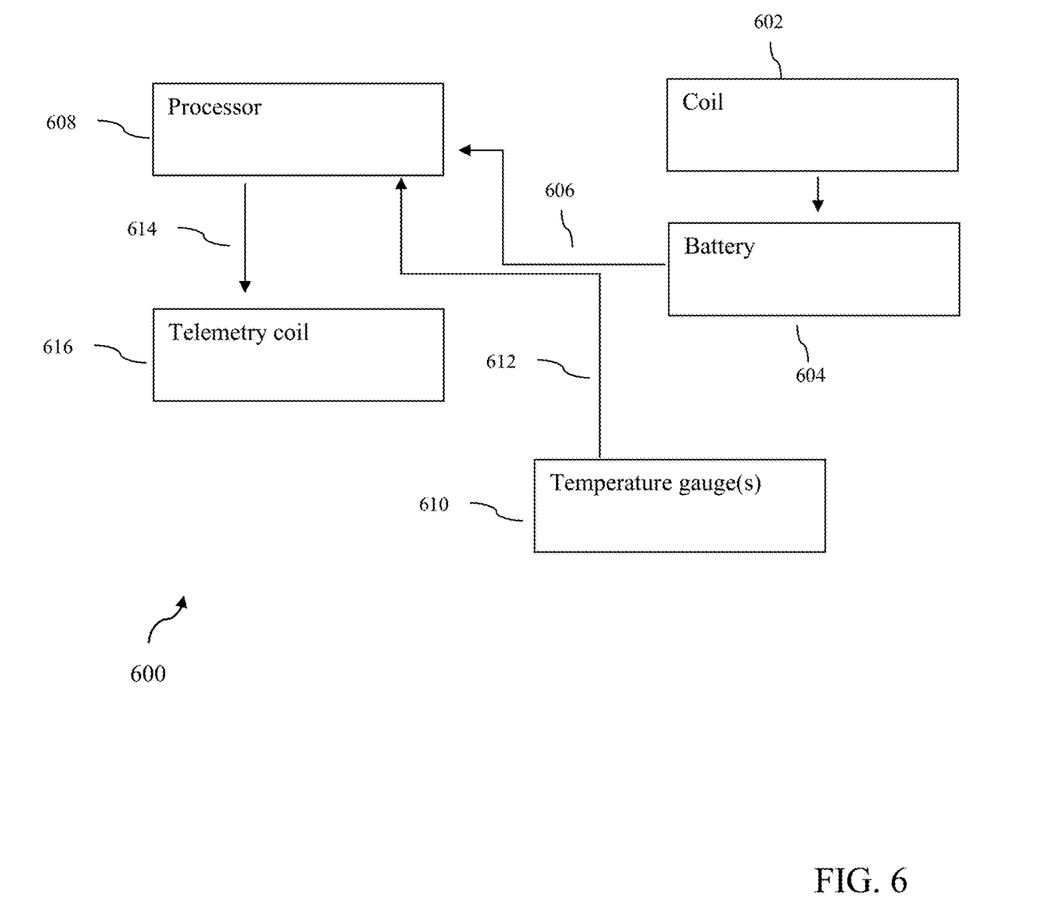
FIG. 6 is a block diagram of a device for managing temperature in a wireless recharge system, according to an embodiment.

FIG. 6 is a schematic diagram of a receiving device 600 for implementing the charging models described herein. Device 600 includes a coil 602 for charging an implantable device. Coil 602 receives electromagnetic signal from a remote emitter (e.g., 102, 302). The coil 602 is electrically coupled via a circuit to a battery 604, and provides charge current thereto. Those reasonably skilled in the art will understand that a rectification circuit may be used to translate the induced signal on the receiver coil and rectification circuitry 602 into useful power into the battery 604.

The level of charge current is transmitted, as indicated by arrow 606, to a processor 608. Temperatures gauge(s) 610 also produce temperature data that is transmitted to the processor 608 as indicated by arrow 612. Based on these charge current and temperature data 608 and 612, processor 608 sends a signal 614 to a telemetry coil 616 that is in communication with the emitter to adjust the recharge electromagnetic field.

As indicated at 616, the telemetry coil 616 and the receiving coil and rectification circuit 602 may be the same coil, in embodiments. In other embodiments, the signal 614 can be used to shut off a switch or otherwise stop coil 602 from generating additional charge current, rather than sending signal back to the emitter directly.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A wireless recharging system for an implantable medical device, the wireless recharging system comprising:
   a plurality of temperature sensors each arranged at one of a corresponding plurality of known locations within a housing of the implantable medical device;
   an antenna electrically coupled to a battery of the implantable medical device, wherein the antenna is configured to provide a level of charge current to the battery upon receiving an electromagnetic field;
   a processor, wherein:
      each of the plurality of temperature sensors is communicatively coupled to the processor to provide temperature data for each of the corresponding plurality of known locations;
      the processor is configured to:
         apply the temperature data from the plurality of known locations to determine heat transfer characteristics for materials external to the medical device and
         operate the antenna dynamically based upon a temperature model that includes the determined heat transfer characteristics for at least one material external to the medical device,
   wherein the temperature model includes thermal transfer characteristics of the at least one material external to the housing and wherein the processor is further configured generate the temperature model by determining the thermal transfer characteristics of the at least one material external to the housing based upon the level of heat dissipation at the plurality of portions of the housing.

2. The wireless recharging system of claim 1, wherein the plurality of temperature sensors comprises at least four sensors and the temperature model is representative of the dissipation of heat caused by providing the level of charge current.

3. The wireless recharging system of claim 2, wherein the processor is located in an device external to the medical device and configured to receive the temperature data wirelessly from the medical device.

4. The wireless recharging system of claim 1, wherein the processor is configured to determine a temperature at each of a plurality of regions of the housing based on the temperature model and the temperature data from the plurality of temperature sensors.

5. The wireless recharging system of claim 1, wherein the temperature model includes thermal resistance characteristics of a plurality of materials in the system.

6. The wireless recharge system of claim 4, wherein a corresponding material for each one of a plurality of regions has a corresponding thermal conductivity, such that a thermal transfer characteristic varies between the plurality of regions.

7. A wireless recharge system comprising:
   a wirelessly rechargeable, implantable medical device including:
      a plurality of temperature sensors each arranged at a corresponding location within a housing such that the thermal resistance between the plurality of corresponding locations is known;
      a receiver coil circuit electrically coupled to a battery, wherein the receiver coil circuit is configured to provide a level of charge current to the battery upon receiving an electromagnetic field;
      a telemetry module configured to send data; and a processor, wherein:
- each of the plurality of temperature sensors is electronically coupled to the processor to provide temperature data;
- the processor is configured to determine the level of charge current;
- the processor is configured to apply the temperature data from the plurality of corresponding locations to determine heat transfer characteristics for materials external to the medical device; and
- the processor is configured to dynamically produce a signal that can operate an emitter coil based upon a temperature model generated from the determined level of heat dissipation at a plurality of portions of the housing; and an emitter including:
- the emitter coil configured to generate a varying electromagnetic field; and
- a telemetry module configured to receive the signal from the telemetry module of the wirelessly rechargeable device.

8. The wireless recharge system of claim 7, wherein the telemetry module is further configured to receive data.

9. The wireless recharge system of claim 7, wherein the emitter is configured to operate the emitter coil output based on the signal from the telemetry module of the wirelessly rechargeable device to prevent the wirelessly rechargeable device from exceeding a predetermined temperature at the housing.

10. The wireless recharge system of claim 9, wherein the processor is configured to determine a temperature at each of a plurality of regions of the housing based on the temperature model and the plurality of temperatures.

11. The wireless recharge system of claim 7, wherein the temperature model includes thermal resistance characteristics of a plurality of materials in the system.

12. The wireless recharge system of claim 10, wherein the device is implanted such that each one of the plurality of regions on the housing is adjacent to a corresponding material, and wherein the corresponding material for each one of the plurality of regions has a corresponding thermal conductivity, such that a thermal transfer characteristic varies between the plurality of regions.

13. The wireless recharge system of claim 7, wherein the plurality of temperature sensors comprises at least four sensors.

14. The wireless recharge system of claim 7, wherein the emitter includes a plurality of temperature sensors, and wherein the telemetry module of the emitter is configured to send data corresponding to each of the plurality of temperature sensors of the emitter to the processor of the wirelessly rechargeable device.

15. The wireless recharge system of claim 14, wherein the model is based on the temperature sensed by the plurality of temperature sensors of the emitter and the plurality of temperature sensors of the wirelessly rechargeable device.

16. A method of wirelessly recharging an implantable medical device, the method comprising:
- detecting a temperature within a wirelessly rechargeable device using a plurality of temperature sensors arranged at a plurality of locations having known thermal resistances therebetween, wherein the plurality of temperature sensors are arranged in the device and the device exhibits time-variant heat dissipation at an external boundary thereof;
- determining a model for heat dissipation around the wirelessly rechargeable device based upon the known thermal resistances and the temperature detected at the plurality of temperature sensors, wherein the model for heat dissipation is based upon time-variant thermal boundary conditions at the external boundary; and
- dynamically determining a charge power level for the emitter coil to maintain a temperature at the external boundary that is lower than a predetermined maximum, based upon the model for heat dissipation.

17. The method of claim 16, further comprising detecting a temperature within an emitter and transmitting the detected temperature within the emitter to the wirelessly rechargeable device.

18. The method of claim 17, wherein the model for heat dissipation is based on both time-variant and time-invariant thermal boundaries.

* * * * *